US00PP35107P2

(12) United States Plant Patent
Skelton

(10) Patent No.: US PP35,107 P2
(45) Date of Patent: Apr. 18, 2023

(54) ***ACTINIDIA CHINENSIS* PLANT NAMED 'H14'**

(50) Latin Name: *Actinidia chinensis*
Varietal Denomination: H14

(71) Applicant: Donald Skelton, Waimate North (NZ)

(72) Inventor: Donald Skelton, Waimate North (NZ)

( * ) Notice: Subject to any disclaimer, the term of this patent is extended or adjusted under 35 U.S.C. 154(b) by 0 days.

(21) Appl. No.: 17/705,720

(22) Filed: Mar. 28, 2022

(51) Int. Cl.
*A01H 6/00* (2018.01)
*A01H 5/08* (2018.01)

(52) U.S. Cl.
USPC ..... Plt./156

(58) Field of Classification Search
USPC ..... Plt./156
CPC ..... A01H 6/00; A01H 5/08
See application file for complete search history.

(56) References Cited

PUBLICATIONS

Chat et al. Proceedings: Biological Sciences, vol. 270, No. 1517, p. 783-789 (Year: 2003).*

* cited by examiner

*Primary Examiner* — Keith O. Robinson
(74) *Attorney, Agent, or Firm* — Cassandra Bright

(57) ABSTRACT

A new and distinct *Actinidia chinensis* plant named 'H14' is disclosed, characterized by large ovoid-shaped fruit with a distinctive soft protrusion of the stylar end. Fruit flesh is yellow. The new variety bears fruit during the early season. The new variety is suitable for commercial production of kiwi fruit.

2 Drawing Sheets

Figure 1:
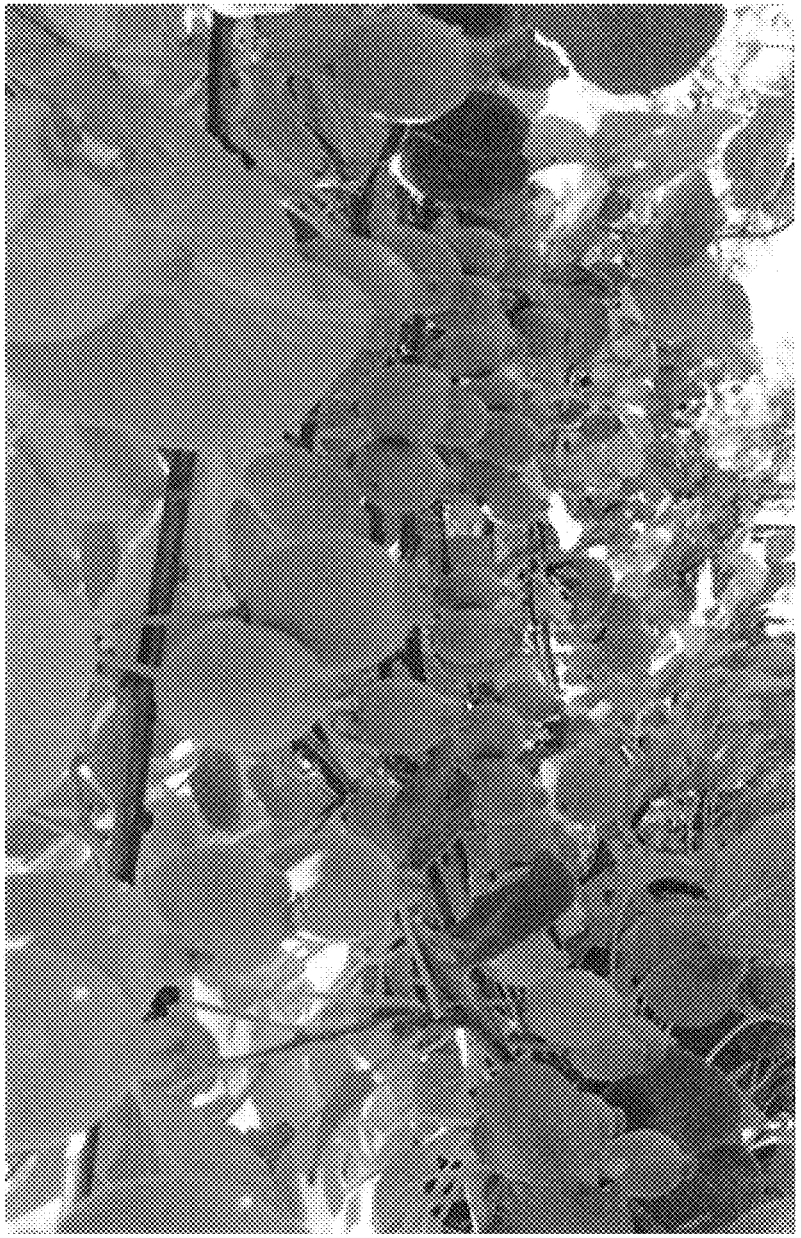

Latin name of the genus and species: *Actinidia chinensis*.
Variety denomination: 'H14'.

BACKGROUND OF THE INVENTION

The new cultivar is a product of a planned breeding program under the direction of the inventor, Donald Alfred Skelton, a citizen of New Zealand. The seed parent is the unpatented, proprietary seedling variety *Actinidia chinensis* 'X365'. The pollen parent is the unpatented, proprietary seedling variety referred to as *Actinidia chinensis* 'Y361'. The crossing was made by the inventor during 2012.

Fruit of the new variety was first evaluated in 2014 with favorable results. After the first evaluation, semi-hardwood cuttings were made of 'H14' and were grafted onto seedling rootstocks of *A. deliciosa*. Evaluation, asexual propagation and grafting all first took place at a research nursery in North Waikato, New Zealand. Subsequent evaluations of the variety have shown the characteristics to be true to type.

SUMMARY OF THE INVENTION

The cultivar 'H14' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'H14'. These characteristics in combination distinguish 'H14' as a new and distinct *Actinidia chinensis* cultivar:

1. Large fruit.
2. Soft protrusion of the stylar end.
3. Yellow fruit flesh.
4. Soft, sparse hair on fruit skin.

4. Early-season harvest.
5. Ovoid fruit shape.

PARENT COMPARISON

The new variety is similar to the seed parent variety in some horticultural characteristics. However, the new variety differs in the following;

1. The new variety produces larger fruit than the seed parent.
2. The new variety produces fruit with a soft protrusion of the stylar end, a characteristic not found in the seed parent variety.

The new variety can be compared to the pollen parent variety, however, the plants clearly differ, as the new variety is a fruit producing female plant and the pollen parent is a non-fruiting male plant. Additionally, the new variety differs in the following;

1. No fruit is produced by the pollen parent.

COMMERCIAL COMPARISON

The new variety is best compared to the commercial variety, 'ZESY002', U.S. Plant Pat. No. 22,355. 'H14' is similar to 'ZESY002' in many horticultural characteristics, however, 'H14' differs in the following:

1. Fruit of the new variety is somewhat larger than fruit of this comparator.
2. The new variety flowers early-season, this comparator flowers late season.
3. The new variety produces fruit with an ovoid shape; fruit shape of this comparator is spherical.

The new variety can be compared to the commercial variety 'Haywood', unpatented. 'H14' is similar to 'Haywood' in many horticultural characteristics, however, 'H14' differs in the following:

1. The new variety flowers early-season, this comparator flowers late season.
2. The new variety produces mature fruit early-season, this comparator produces mature fruit late season.
3. The new variety produces fruit with gold colored flesh; this comparator produces fruit with green colored fruit.
4. Fruit of 'H14' has minimal hair on the fruit; this comparator produces fruit with abundant pubescence.

BRIEF DESCRIPTION OF THE PHOTOGRAPHS

The accompanying photograph in FIG. 1 illustrates in full color examples of typical fruits of 'H14', while on the plant, as well as typical foliage. This figure illustrates the heavy bearing characteristics of the variety.

Figure 2:
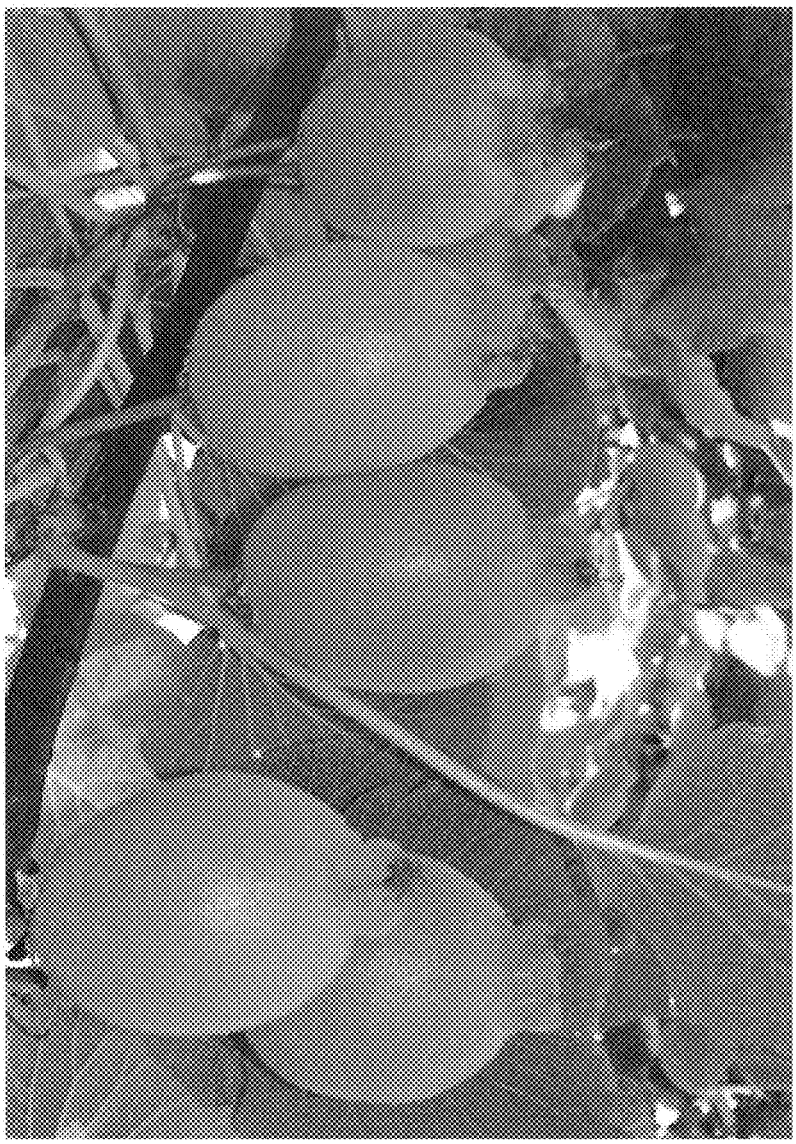

FIG. 2 illustrates a closer view of typical fruit of 'H14' on the plant, including the distinct stylar protrusion. Plants depicted are approximately 5 years old.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'H14' plants grown outdoors under commercial trial conditions in Rangiriri, New Zealand. The growing temperature ranged from 10° C. to 30° C. during the day and −3° C. to 15° C. at night. Annual rainfall is approximately 125 cm per year. Measurements and numerical values represent an average of 10 typical plant types, measurements of foliage taken from mid June to mid August.

Botanical classification: *Actinidia chinensis* 'H14'.

Propagation: 'H14' can be successfully grafted onto rootstocks of *Actinidia deliciosa.*

Plant:

*Age of the plant described.*—Approximately 3 years.
*Sex expression.*—Female.
*Ploidy.*—Diploid.
*Average height.*—2 m.
*Average width.*—4 m.
*Vigor.*—Average to strong.
*Young shoot color.*—Near RHS Yellow-Green 140C.
*Young shoot texture.*—Very softly pubescent.
*Mature branch/shoot diameter.*—Average 1.5 cm.
*Mature branch/shoot length.*—Average 200 cm.
*Mature branch/shoot texture.*—Smooth.
*Young shoot hair density.*—Medium.
*Stem lenticels description.*—Length: Average 2.4 mm. Width: Average 1 mm. Density: Approximately 2 per 5 cm of stem.
*Stem pith.*—Solid, firm.
*Stem thickness.*—Medium.
*Bud support of the stem.*—Weak.
*Bud cover of the stem.*—Absent.
*Leaf scar.*—Moderate.
*Trunk diameter.*—Approximately 4.0 cm for a 3-year-old plant.
*Trunk texture.*—Rough.
*Trunk color.*—Near RHS Grey-Brown 199B.

Foliage:

Leaf:

*Average length.*—Average range from 10 cm to 12 cm.
*Average width.*—Average range from 12 cm to 14 cm.
*Shape of blade.*—Cordate.
*Apex.*—Retuse.
*Base.*—Cordate.
*Basal lobes.*—Touching each other.
*Margin.*—Slightly ciliate.
*Texture of top surface.*—Leathery.
*Texture of under side.*—Soft but non-pubescent.
*Color.*—Mature foliage upper side: Near RHS Green 136A. Mature foliage under side: Near RHS Yellow-Green 147C.
*Petiole.*—Length: 8 cm to 13 cm. Pubescence: Sparse, short pubescence. Color: Near RHS 142C. Red-Purple 59C.

Flower:

*Flowers per inflorescence.*—1 to 3.
*Flower shape.*—Hemispherical.
*Bud color.*—Near RHS 145B.
*Bud shape.*—Oblong.
*Bud break.*—Early.
*First flower.*—Last week of September in Rangiri, New Zealand.
*Diameter.*—Average 5 cm.
*Depth.*—Average 3 cm.
*Petal quantity.*—7.
*Petals overlapping.*—Yes.
*Petals.*—Length: Approximately 1.5 cm. Width: Approximately 0.5 cm. Shape: Spatulate. Aspect: Slightly undulating. Margin: Entire, with infrequent irregular shallow crenations. Texture: Glabrous, all surfaces. Base: Attenuate. Apex: Retuse.
*Petals.*—Color: Upper Surface: Near RHS Yellow-White 158D. Lower Surface: Near RHS Yellow-Green 146D.
*Filament color.*—Near RHS 157D.
*Anther color.*—Near RHS Yellow-Orange 15C.
*Attitude of styles.*—Erect.
*Style color.*—Near RHS 155D.
*Style quantity.*—Average 33.
*Hair on ovary.*—Dense.
*Color of ovary.*—Near RHS White 155D.
*Number of sepals.*—Average 7.
*Color of sepals.*—Near RHS Yellow-Green 154A.
*Sepal width.*—Approximately 5 mm.
*Sepal length.*—Approximately 7 mm.
*Sepal texture.*—Smooth.
*Sepal shape.*—Deltate.
*Sepal margin.*—Entire.
*Sepal apex.*—Acute.
*Sepal base.*—Truncate.

Peduncle:

*Length.*—Average 5.5 cm.
*Diameter.*—Average 0.3 cm.
*Color.*—Near RHS 144B.
*Texture.*—Smooth.

Fruit:

*Average weight.*—125 grams.
*Minimum weight.*—110 grams.
*Maximum weight.*—155 grams.
*Average length.*—10 cm.
*Average diameter.*—6 cm.
*Color outer pericarp.*—Near RHS Yellow 10D.

*Color inner pericarp*.—Near RHS Yellow 10C.
*Color of fruit locules*.—Near RHS Yellow 10C.
*Core color*.—Near RHS Yellow 8C.
*Core diameter*.—Average 1.8 cm.
*General shape*.—Ovoid.
*Brix at consumption*.—18.
*Brix at harvest*.—8.0 to 9.0.
*Fruit peduncle length*.—55 mm.
*Fruit peduncle width*.—3 mm.
*Median cross section*.—Ovoid.
*Stylar end shape*.—Soft blunt protruding.
*Shoulder shape*.—Square, truncate.
*Calyx ring*.—Present, circular.
*Calyx ring expression*.—Weak.
*Skin color at harvest*.—Near RHS 152B.
*Hair on fruit skin*.—Soft, sparse.
*Hair adherence to skin*.—Weak.
*Skin adherence to flesh at maturity*.—Moderate.
*Fruit core shape*.—Transverse elliptic.
*Core-woody spike*.—Minor.
*Lenticels on fruit*.—None.
*Mature seed color*.—Near RHS Black 202A.
*Harvest time*.—April (Southern Hemisphere, Rangiriri, New Zealand)
*Overall cropping quantity*.—45 to 50 tonnes per hectare.

Fruit stem:
*Length*.—Average 46 mm to 60 mm. Average 54 mm.
*Diameter*.—Average 3 mm.
*Color*.—Near RHS Grey-Brown 199B.
*Texture*.—Smooth.

Other characteristics:
Storage life: Storage life is a minimum of 175 days at 2° C.
Disease/pest resistance: Neither resistance nor susceptibility to pathogens and pests common to *Actinidia chinensis* have been observed.
Temperature tolerance: Tolerates low temperatures to approximately −5° C. without negative effects, tolerates high temperatures to approximately 35° C. without negative effects.

What is claimed is:

1. A new and distinct cultivar of *Actinidia chinensis* plant named 'H14' as herein illustrated and described.

* * * * *